United States Patent [19]

Nemec et al.

[11] 4,021,368

[45] May 3, 1977

[54] PROCESS OF TREATING MYCELIA OF FUNGI FOR RETENTION OF METALS

[75] Inventors: Pavel Nemec, Bratislava; Hubert Procházka, Brno; Karel Štamberg, Prague; Josef Katzer, Prague; Jiří Štamberg, Praha; Rudolf Jílek, Brno; Pavel Hulák, Ceske Budejovice, all of Czechoslovakia

[73] Assignee: Ceskoslovenska komise pro atomovou energii Praha, Prague, Czechoslovakia

[22] Filed: Jan. 20, 1975

[21] Appl. No.: 542,515

Related U.S. Application Data

[63] Continuation-in-part of Ser. No. 331,659, Feb. 12, 1973, abandoned.

[52] U.S. Cl. .............................. 252/427; 210/38 B; 195/54
[51] Int. Cl.² ..................... B01D 15/00; C02B 1/14
[58] Field of Search ............... 195/1, 28 R, 81, 52, 195/53, 54, 55, 56; 210/38 B, 503, 504; 252/427

[56] References Cited

UNITED STATES PATENTS

| | | | |
|---|---|---|---|
| 3,725,291 | 4/1973 | Serbus et al. | 210/38 |
| 3,767,790 | 10/1973 | Guttag | 195/54 |
| 3,859,210 | 1/1975 | Hatch | 210/38 |

Primary Examiner—Alvin E. Tanenholtz

[57] ABSTRACT

Biomasses of mycelia of microorganisms, particularly of fibrous fungi used for retention of metal ions from solutions, particularly of uranium, radium, lead and similar are stiffened by adding polymerizable components to them by polymerization, and the product is subsequently mechanically granulated. The granulated product is then employed in cyclically repeated sorption processing of heavy metal ions by contacting it with solutions of such metals.

7 Claims, No Drawings

PROCESS OF TREATING MYCELIA OF FUNGI FOR RETENTION OF METALS

This application is a continuation-in-part of application Ser. No. 331,659, filed on Feb. 12, 1973.

BACKGROUND OF THE INVENTION

This invention relates to a process of a chemical and physical treatment of a mycelium which is in a natural or dry condition or has been treated by crushing, and to a process of treating solutions of heavy metals thereby. The mycelium may belongto different kinds of microorganisms, particularly of fibrous fungi capable of retention of metals such as uranium, lead, radium and others from their solutions. The retention mechanism may be for instance based on sorption.

It has already been proposed to apply the mycelium of some kind of lower fungi, advantageously of waste mycelium in the fermenting and pharmaceutical industry for removal of uranium, of elements of the uranium-radium type, of lead and other metals. This material has a good capacity and selectivity but has a drawback in having a low mechanical rigidity; this causes difficulties in the retention or sorption process by means of a column or by other modifications of dynamic sorption in industrial operation. This holds true for both for filtered native mycelium and for dried mycelium.

SUMMARY OF THE INVENTION

We have found that this drawback can be eliminated by a suitable stiffening of the supporting skeleton of the mycelium which is predominantly composed of polymers of the polysaccharide type.

According to this invention, the mycelium is stiffened by suitable chemical adjustment, particularly by the cross-linking of its macromolecular structure, by stiffening by high molecular material or by both methods simultaneously.

In a convenient arrangement of this adjustment, the active centers capable of selectively bonding with above mentioned heavy metal ions remain practically untouched, in the original mycelium, resulting in the maintenance of their capacity and of other sorption properties.

The method of chemical adjustment has to be chosen so as to correspond to the chemical structure of the mycelia, that is, to their polysaccharide and polypeptide components. It is possible to use as polymerizable components formaldehyde and further monofunctional aldehydes, glyoxal, glutaraldehyde, or other polyfunctional aldehydes, for instance, a solution of polyacroleines in sulphurous acid. Similar results are obtained with diisocyanates, or with epichlorhydrine, dichlorhydrines, chlorides of dicarboxyl acids and others. Improvements in the mechanical properties of the mycelium can be also obtained by application of natural or artifial pickling agents, for instance, by polyvalent phenols or by chromium salts.

Furthermore, a number of natural high molecular materials can be used for stiffening of the mycelium. Gelatine can, for instance, be used from the polypeptides. It can be applied in the form of aqueous solutions and is subsequently cured by formaldehyde. Similarly, it is possible to apply casein (for instance disolved in lye), different glues, zein, albimin and other polypeptidic materials. From the polysaccharides starch or its hydrolytic products in aqueous solutions or cellulose (dissolved for instance in Schweitzer's agent can be used, or as xantogenate) which can be subsequently stiffened by the action of diisocyanates, epoxycompounds, dialdehydes, chlorides of dicarboxyl acids and similar. From starch derivatives there can be used, for instance, its oxidized form with aldehydic groups. Other advantageous natural materials are also pectins, gums, and slimes (arabic gum, agaragar and others), dextrates, lignin, or its derivatives.

Synthetic materials capable of forming high molecular structures, advantageously having hydrophylic properties, are equally suitable for the stiffening of mycelia. These particularly include phenols, amines, or their derivatives, multivalent phenols and amines, or derived compositions also containing carboxyl groups. It is also possible to "saturate" the mycelia by these materials and start their polycondensation by an addition of formaldehyde. Other monofunction or polyfunction aldehydes (such as actealdehyde, glyoxal, glutaraldehyde and others) urotropin, diisocyanates, epoxide compositions and others can be used besides formaldehyde. Hydrophilic groups (sulphon, amine groups) can be introduced into the structure also in the course of the polycondensation, for instance by sulphomethylation or aminoethylation. Urea is also suitable in addition to amines and phenols, or methylureas, thiourea, melanin, dicyandiamide, guanidin and their derivatives. Another suitable material is plyvinylacetate hydrolized to a different degree, or completely hydrolyzed to polyvinylalcohol. (In order to increase the insolubility, tempering can be applied by the action of phosphoric acid, diisocyanates, chlorides or anhydrides of polycarboxylic acid, polyaldehydes, trimethylpropane and similar. Another group of materials suitable for stiffening mycelia are acrylic acid, methacrylic acid, their esters (for instance glycolmethacrylate, glycidylmethacrylate and similar), amides, nitriles and similar materials. These monomers are mixed in order to increase the insolubility with polyvinyl components such as divinylbenzene, ethyldimetacrylate and similar, or the finished polymers are cross-linked additionally, for instance, by the action of formaldehyde or polyacrylamide. A suitable stiffening component is also ethylenimin, or polyethylenimin combined, for instance, with polyaldehydes. Other groups of materials suitable for stiffening of mycelia are polyurethanes, polyureas and epoxides resins.

EXAMPLES OF THE PROCESS

EXAMPLE 1

8 g of dried mycelium of the strain Penicillium chrysogenum was mixed with 4.9 ml of water, 0.1 g sodium hydroxide and 3.54 ml of 35% formaldehyde was added and boiled under a reflux condenser for 1 hour. After cooling, a solution containing 2 g of resorcinol, 4.9 ml of water and 3.54 ml of 35% formyldehyde was added. The mixture was left standing after mixing at simultaneous heating to 70° C. It was thereafter heated under continuous mixing to 80° C whereby condensation proceeded to a dull red liquid, which condensed fully in a drying chamber at a temperature of 105° C. The product was crushed to a grain size of 0.3 to 0.75 mm. The capacity of the sorbent for uranium was 95.7 mg/g.

(The capacity for uranium was determined by a static method in all mentioned examples as follows: 1 g of the sorbent was shaken for 16 hours with 100 ml of a solution $UO_2(NO_3)_2$ having a concentration of uranium of 1 g/l, the capacity being calculated from the decrease of uranium in the solution).

EXAMPLE 2

4 g of dried mycelium of the strain P chrysogenum was mixed with a solution containing 5 ml water, 0.08 sodium hydroxide and 3.6 ml formaldehyde and boiled under a reflux condenser for 1 ½ hour. Then 0.5 ml concentrated hydrochloric acid was added slowly, cooled down and the obtained precondensate triturated in a dish. It was subsequently rinsed by 3.6 ml of 35% formaldehyde into a dish and under effective cooling a solution of 2 g m-phenylendiamine in 5 ml water acidified by 1.65 ml of hydrochloric acid was added at once. The condensation took place in the course of about 45 seconds at creation of red-brown liquid, which condensed fully in a drying chamber at 105° C. The product was crushed to a grain size of 0.3 to 0.75 mm.

The capacity of the sorbent for uranium was 39.3 mg/g.

EXAMPLE 3

6.9 g or urea was dissolved in 30 ml water and 15 g 35% formaldehyde was added with the pH value adjusted to 7.5 by a sodium lye. 27.6 g of mycelium P chrysogenium in crushed shape was added and the whole was heated in an aqueous bath for about 2 hours. After transfer to a porcelain dish, 2 ml of concentrated acetic acid was added into the precondensate and the final condensation proceeded in a drying chamber at a temperature of 90° to 105° C in the course of 2 to 2 ½ hours. The product was crushed to a grain size of 0.3 to 0.75 mm.

The capacity of the sorbent for uranium was 92.1 mg/g.

EXAMPLE 4

5 g of a precondensate of an epoxide resin having the commercial designation Epoxy 1200 was mixed with 10 g of a curing agent of the commercial design P1. The originating paste-like suspension was converted to a solution by 10 ml of acetone, with which 25 g of mycelium P chrysogenium, prior prepared to a grain size about 0.3 to 0.5 mm was impregnated. The acetone was distilled away by heating, and the curing was finished in a drying chamber at a temperature of 100° C. The individual particles from a compact highly porous block, which is crushed relatively easily to the original grain size. (The grain size is eventually adjusted by shifting). The capacity of the sorbent for uranium is 94.1 mg/g.

EXAMPLE 5

15 g of finely crushed mycelium of the strain P chrysogenum was mixed in a tritutated dish with 10 ml of water and 10 g polyvinylacetate emulsion (content in the dry form was 54.8 %). A mass of paste-like consistency was thus created, which was perfectly homogenized by a pestle and subsequently cured in a drying chamber at a temperature of about 100° C. The product was crushed to a grain size of 0.3 to 0.75 mm.

Capacity of the sorbent for uranium was 69.4 mg/g.

EXAMPLE 6

5 g of gelatine was dissolved in 30 ml water (by beating in an aqueous bath) and 15 g moistened, finely triturated mycelium of the strain P chrysogenum was added. A mass of paste-like consistency was obtained, which was perfectly homogenized and kneaded in a trituration dish. 5 ml of 35% formaldehyde was subsequently added and again kneaded. The curing was performed in a drying chamber at a temperature of about 100° C. The hardened product was crushed and sifted to a grain size of 0.3 to 0.75 mm.

The capacity of the sorbent for uranium was 100.9 mg/g.

EXAMPLE 7

4 g of bone glue was dissolved in 30 ml of heated water and 16 g of mycelium of the strain P chrysogenum was added to the solution. After perfect homogenizing in a trituration dish, 5 ml of 35% formaldehyde was added, the mixture was kneaded, and was cured in a drying chamber at a temperature of about 100° C. The product was crushed to a grain size of 0.3 to 0.75 mm. The capacity of the sorbent for uranium was 102.5 mg/g.

EXAMPLE 8

5 g of wheat starch was mixed with 10 ml of water at room temperature, then poured into 20 ml of boiling water. The created starch paste was "triturated" with 15 g of finely triturated mycelium of the strain P chrysogenum, which has to be moistened prior to introduction into the starch paste. The mass of paste-like consistency was cured in a drying chamber for about 10 hours at a temperature of 90° to 100° C. The product was crushed to a grain size of 0.3 to 0.75 mm.

The capacity of the sorbent for uranium was 88.9 mg/g.

EXAMPLE 9

5 g of casein was rinsed with 10 ml of water, left about 1/2 hour to swell, then 15 g of finely crushed and moistened mycelium of the strain P chrysogenum and 5 ml of 35% formaldehyde were added and everything was perfectly homogenized in a trituration dish. The mixture gradually thickened to a homogeneous thick paste. The curing was finished in a drying chamber at a temperature of 100° C. The product was crushed to a grain size of 0.3 to 0.75 mm. The capacity of the sorbent for uranium was 92 mg/g.

EXAMPLE 10

30 g of mycelium of the strain P chrysogenum was introduced into 150 ml of 35% formaldehyde, to which has been prior added 1.5 g sodium hydrozide. (The mycelium had been adjusted to a grain size of 2 to 3 mm). The mixture was maintained boiling in a flask with a reflux condenser for about 2 hours. Then the liquid phase was decanted and the solid phase washed on a filter with water. The curing was finished in a drying chamber at a temperature of about 100° C. The grain size of the product was adjusted to 0.3 to 0.75mm.

The capacity of the sorbent for uranium was 98.5 mm/g.

When polymerization is mentioned in the specification or claims, this term is intended to include not only polymerization on double bonds, but also any other reaction by which polymers originate from low molecular starting material, such as polycondensation, polyaddition, and similar actions.

Under the term "native" such a state of mycelium is to be understood which is characteristic for the cultivation, growth and the like stage thereof, which means that mycelium in a fermentor (or immediately withdrawn therefrom) can be called as native mycelium, in contradistinction to dried mycelium in which all the biological and biochemical processes have been interrupted and finished.

The term "biomass" is to be understood as a generic term for mycelium, i.e. both native and dried mycelium; the composition of biomass is characterized or influenced by the conditions of preparing the same, such as, for instance, cultivation period, temperature, composition of nutrients medium, temperature and method of drying, etc.

Although the invention is illustrated and described with reference to a plurality of preferred embodiments thereof, it is in no way limited to the disclosure of such a plurality of preferred embodiments thereof, but is capable of numerous modifications within the scope of the appended claims.

What is claimed is:

1. A process of treating as biomass the mycelia of microorganisms to produce a stiffened essentially water-insoluble granulated product for application for the industrial retention from solutions of heavy metal ions chosen from the group consisting of uranium, radium, and lead by cyclically repeated sorption processing of such heavy metal ions by contacting it with solutions of such metal ions, comprising mixing the biomass with at least one polymerizable stiffening component capable of forming a polymeric system in a weight ratio of 1 part biomass to 0.1 - 3 parts stiffening component, polymerizing the biomass and stiffening component mixture to produce a stiffened essentially water-insoluble product, drying the stiffened product, the polymerizing and drying steps being carried out at a temperature of about 90° - 105° C and granulating the resulting dried stiffened product.

2. A process as in claim 1, comprising employing the granulated stiffened product in cyclically repeated sorption processing of heavy metal ions by contacting it with solutions of such metal ions.

3. A process as in claim 2, wherein the polymerizable stiffening component is chosen from the group consisting of formaldehyde, resorcinol, urea, m-phenyldiamine, gelatine, starch, bone glue, casein, epoxide resin and acrylic resin.

4. A process as in claim 3, wherein the acrylic resin is chosen from the group consisting of polyglycol methacrylates, polyacrylamides, polymethacrylamides and copolymers thereof.

5. A process as in claim 2, wherein the mycelia of microorganisms are of the fibrous fungi of the strain Penicillium Aspergillus.

6. A process as in claim 5, wherein the mycelia of microorganisms is in the natural condition.

7. A process as in claim 5, wherein the mycelia of microorganisms is in a dry condition.

* * * * *